United States Patent [19]

Pospisil et al.

[11] Patent Number: 5,597,302
[45] Date of Patent: Jan. 28, 1997

[54] AESTHETIC PLASTIC ORTHODONTIC BRACKET WITH LOAD BEARING FRAMEWORK

[75] Inventors: Jirina V. Pospisil, Covina; James D. Hansen, Duarte; James D. Cleary, Glendora, all of Calif.

[73] Assignee: Minnesota Mining and Manufacturing Company, St. Paul, Minn.

[21] Appl. No.: 322,988

[22] Filed: Oct. 14, 1994

[51] Int. Cl.[6] ................................................ A61C 3/00
[52] U.S. Cl. ............................................................. 433/8
[58] Field of Search .................................. 433/8, 9, 10

[56] References Cited

U.S. PATENT DOCUMENTS

| | | | |
|---|---|---|---|
| D. 315,957 | 4/1991 | Kelly et al. ........................ | D24/16 |
| 2,908,974 | 10/1959 | Stifter . | |
| 3,250,003 | 5/1966 | Collito ............................... | 32/14 |
| 3,303,565 | 2/1967 | Newman . | |
| 3,423,833 | 1/1969 | Pearlman . | |
| 3,464,112 | 9/1969 | Silverman et al. . | |
| 3,469,314 | 9/1969 | Pearlman . | |
| 3,504,438 | 4/1970 | Wittman et al. . | |
| 3,922,787 | 12/1975 | Fischer et al. .................... | 433/8 |
| 3,930,311 | 1/1976 | Andrews . | |
| 3,964,165 | 6/1976 | Stahl . | |
| 4,050,156 | 9/1977 | Chasanoff et al. . | |
| 4,107,844 | 8/1978 | Kurz . | |
| 4,186,488 | 2/1980 | Wallshein ......................... | 433/8 |
| 4,249,897 | 2/1981 | Anderson ......................... | 433/8 |
| 4,299,569 | 11/1981 | Frantz .............................. | 433/8 |
| 4,302,532 | 11/1981 | Wallshein ......................... | 433/8 |
| 4,353,692 | 10/1982 | Karrakussoglu ................. | 433/16 |
| 4,674,978 | 6/1987 | Acevedo ........................... | 433/8 |
| 4,850,865 | 7/1989 | Napolitano ....................... | 433/8 |
| 5,078,596 | 1/1992 | Carberry et al. ................. | 433/8 |
| 5,254,002 | 10/1993 | Reher et al. ..................... | 433/8 |
| 5,358,402 | 10/1994 | Reed et al. ....................... | 433/8 |

OTHER PUBLICATIONS

Image™ advertisement, GAC International, Inc., *Ortho World*, Issue III, vol. XXVII, Fall 1994.
Spirit™ Composite Bracket brochure, Ormco Corporation, copyright date unknown.
EPO Search Report for 08/322,988.

*Primary Examiner*—Cary E. O'Connor
*Attorney, Agent, or Firm*—Gary L. Griswold; Walter N. Kirn; James D. Christoff

[57] ABSTRACT

An orthodontic bracket has a load bearing framework embedded in a plastic body. The framework includes archwire-engaging end portions that are coplanar with a lingual side of an archwire slot. The end portions faciliate control of movement of the bracket and the associated tooth. A buccolabial surface of the bracket is roughened to enhance aesthetics.

18 Claims, 4 Drawing Sheets

AESTHETIC PLASTIC ORTHODONTIC BRACKET WITH LOAD BEARING FRAMEWORK

BACKGROUND OF THE INVENTION

1. Field of the Invention

This invention relates to an aesthetic orthodontic bracket having an archwire-engaging, load bearing framework embedded within a plastic body.

2. Description of the Related Art

Orthodontic treatment concerns movement of malpositioned teeth to orthodontically correct positions. In certain types of orthodontic treatment, tiny, slotted appliances known as brackets are affixed to anterior, bicuspid and cuspid teeth, and other appliances known as buccal tubes are secured to the molar teeth. An orthodontic archwire is placed in the slots of the brackets and is tied in place using small elastomeric O-rings or metallic ligature wires. Ends of the archwire are inserted into channels of the buccal tubes.

As orthodontic treatment progresses, the archwire serves as a track to guide movement of the teeth toward desired positions. Bends, loops or twists are often placed in the archwire to urge movement of the teeth. Alternatively, one or more elastic members secured to brackets or buccal tubes of certain teeth provide a force to move the associated teeth to their correct positions.

Many orthodontic brackets are made of metallic materials such as stainless steel. Metal brackets are often considered to provide satisfactory sliding mechanics, adhesion to teeth and debonding characteristics. However, metal brackets are visible in the oral cavity and often an embarrassment to the patient.

Ceramic brackets made of a color-free, translucent polycrystalline material provide an advantage over metal brackets in that the ceramic material permits the natural color of the tooth to diffusely show through the bracket. Examples of such aesthetic brackets are described in U.S. Pat. No. 4,954,080 which is assigned to the assignee of the present invention.

Orthodontic brackets made of plastic materials are also sometimes considered more aesthetic than metal brackets. Some plastic brackets are essentially color-free, and contain fiber or other filler material that scatters light transmitted through the bracket. Plastic brackets that scatter and diffuse light are often considered more aesthetic than transparent plastic brackets that may glisten and hence be more visible when in use in the oral cavity.

One problem long associated with plastic brackets, however, is the tendency for the plastic to deform or creep in areas surrounding the archwire slot. If the archwire slot widens, precise control over the position of the bracket and hence of the associated tooth is hindered.

Moreover, some plastic brackets are not as strong and resistant to fracture as their metal counterparts. Such plastic brackets may fracture in use, especially in narrow regions of the bracket between the archwire slot and ligature undercut regions located behind tiewings of the bracket. Replacement of the broken brackets is a nuisance to the orthodontist as well as to the patient, and can prolong treatment.

Attempts have been made to improve plastic brackets by use of a metal liner covering the archwire slot opening. An example of such construction is described in U.S. Pat. No. 4,299,569. The metal liner provides metal-to-metal contact between the archwire and the bracket so that the sliding mechanics of the bracket resemble sliding mechanics observed in connection with the use of metal brackets.

However, metal archwire slot liners such as described in U.S. Pat. No. 4,299,569 are not entirely satisfactory. For example, when such brackets are subjected to torquing forces as may occur when an attempt is made to pivot the long axis of the tooth in a direction either toward or away from the tongue, the archwire slot liner may deform along with deformation of the plastic. Once the liner spreads open a sufficient extent and no longer complementally engages sides of the archwire, precise control over movement of the associated tooth is significantly hindered.

A reinforcing framework for plastic brackets is described in U.S. Pat. No. 3,930,311. Such construction is an advantage over plastic brackets having a metal liner, in that the framework stiffens the bracket and is considered to distribute stresses over greater regions of the bracket than plastic brackets having archwire slot liners. In some of the embodiments set out in U.S. Pat. No. 3,930,311, edges of the framework are coplanar with edges of the archwire slot such that the archwire directly contacts the metal framework.

Presently, there is a need in the art for an orthodontic bracket having an embedded framework that efficiently and effectively distributes stresses throughout the plastic body from forces imposed by the archwire, and which also provides improved control of the bracket and the associated tooth during various types of orthodontic treatment. It would also be desirable to provide a plastic bracket having improved aesthetic characteristics in comparison to presently known plastic brackets.

SUMMARY OF THE INVENTION

The present invention is directed toward a plastic orthodontic bracket, and comprises a plastic body having a mesial tiewing section and a distal tiewing section. The body also includes an elongated archwire slot that extends through the mesial tiewing section and the distal tiewing section, and the archwire slot includes a lingual side. A metallic framework is partially embedded in the plastic body. The framework includes a mesial portion extending in the mesial tiewing section in a transverse direction with respect to the longitudinal axis of the archwire slot and a distal portion extending in the distal tiewing section in a transverse direction with respect to the longitudinal axis of the archwire slot. The framework includes an intermediate portion interconnecting the mesial portion and the distal portion. The framework includes a first end portion located mesially of the mesial portion and a second end portion located distally of the distal portion. The first end portion and the second end portion each have a buccolabially-facing surface that is coplanar with the lingual side of the archwire slot.

The first and second end portions of the framework provide enhanced bearing surfaces for an archwire when an archwire is received in the slot. For example, when the archwire imposes forces on the bracket to rotate the tooth about its long axis, the archwire bears against one of the end portions and such bearing forces or stresses are distributed throughout the plastic body. In such an instance, the plastic bracket of the invention functions similar to a metal bracket in that satisfactory control of movement of the bracket and the associated tooth can be achieved without undue deformation, if any, of the archwire slot or other portions of the bracket.

The present invention is also directed toward an orthodontic appliance that comprises a plastic body having a mesial tiewing section, a distal tiewing section and an archwire slot extending through the mesial tiewing section and the distal tiewing section. The body includes an outer, buccolabially-facing surface having a surface roughness of greater than about 43 microinches $R_A$.

In addition, the present invention is directed toward an orthodontic appliance that comprises a plastic body having a mesial tiewing section, a distal tiewing section and an archwire slot extending through the mesial tiewing section and the distal tiewing section. The body includes an outer, buccolabially-facing surface having a surface roughness of greater than about 37 microinches $R_A$ and the body has a haze value of less than about 30%.

DETAILED DESCRIPTION OF THE PREFERRED EMBODIMENTS

An orthodontic appliance 10 constructed in accordance with the principles of the present invention is illustrated in FIGS. 1–5 and is broadly designated by the numeral 10. The appliance 10 that is shown in the drawings for exemplary purposes is an orthodontic bracket, although the invention is equally applicable to other orthodontic appliances such as buccal tubes or bands that are directly bonded to a tooth surface. The appliance 10 includes a plastic body 12 and a metallic framework 14 that is partially embedded in the plastic body 12. The body 12 has a mesial (i.e., in a direction toward the center of the patient's dental arch) tiewing section 16 and a distal (i.e., in a direction away from the center of the patient's dental arch) tiewing section 18.

An elongated archwire slot 20 extends through the sections 16, 18 in a mesial-distal direction. Each of the tiewing sections 16, 18 include an occlusal tiewing (i.e., the tiewing next to the outer tip of the tooth) and a gingival tiewing (i.e., the tiewing next to the patient's gingiva or gums). The occlusal and gingival tiewings are located on opposite sides of the archwire slot 20.

The body 12 includes a bonding base 22 with a lingual surface 23 that faces the tooth to be bonded. The bonding base surface has a contour and optionally a compound contour that closely matches the contour of the portion of the tooth surface that receives the appliance 10.

The bonding base 22 includes a number of spaced apart pegs or projections 24 arranged in a grid-like array. Each projection 24 extends lingually away from the surface 23 and includes a shank preferably having side walls preferably parallel to the mesial, distal, occlusal and gingival sides of the appliance 10. The shank of each projection 24 is slightly larger in cross-sectional area at its base (i.e., next to the surface 23) relative to its outer, lingual end for facilitating removal of the appliance 10 from the mold.

Figure 1:
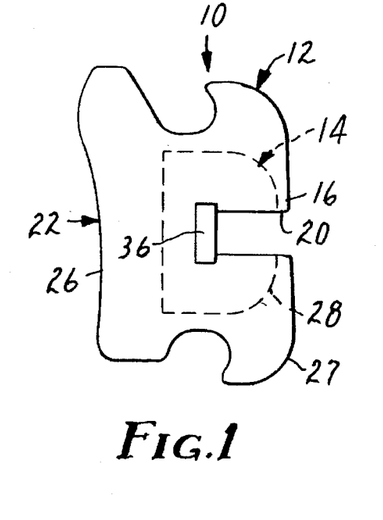
FIG. 1 is an end elevational view of an orthodontic appliance constructed in accordance with the present invention.
Figure 2:
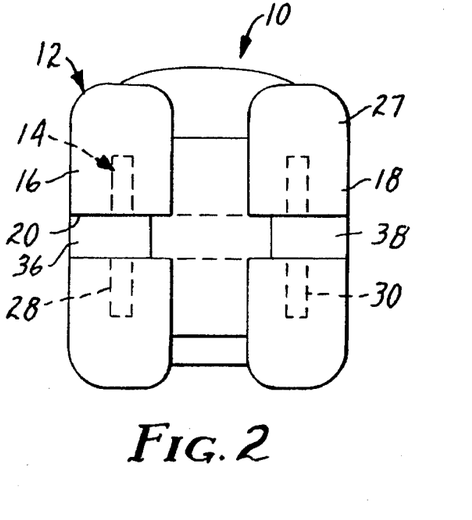
FIG. 2 is a front view looking toward a buccolabial side (i.e., toward a lip or cheek facing side) of the appliance illustrated in FIG. 1.
Figure 3:
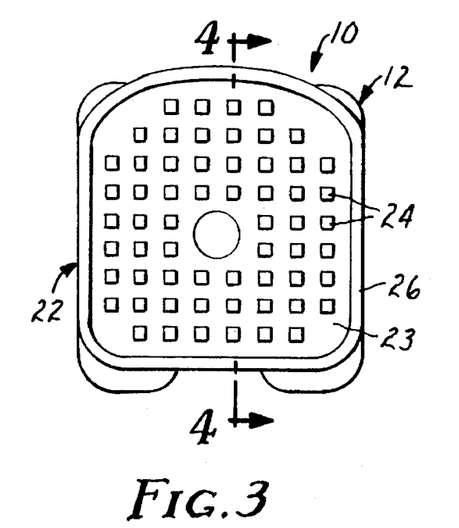
FIG. 3 is a rear view looking toward a lingual or tooth facing side of the appliance illustrated in FIGS. 1 and 2, and wherein a bonding base of the appliance is illustrated during an intermediate step of manufacture.
Figure 4:
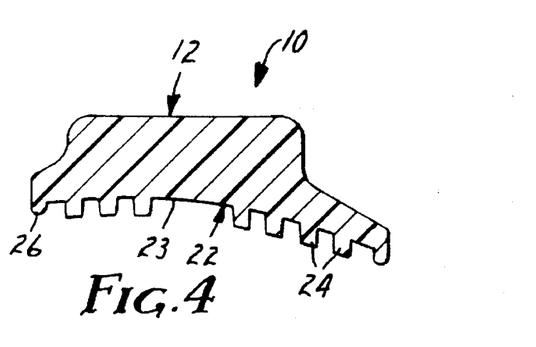
FIG. 4 is an enlarged partial cross-sectional view taken along lines 4—4 of FIG. 3.

A rim 26 extends around the periphery of the bonding base 22 and surrounds the projections 24. As illustrated in FIG. 4, the rim 26 initially has a height in a lingual direction (as measured from the surface 23) that is less than the lingual height of the projections 24. Preferably, the height of each projection 24 in a lingual direction is identical such that the outer edges of the projections 24 lie in a curved reference plane that is identical in contour but slightly spaced from a curved bonding base surface 23.

The body 12 is made of a heat softenable, thermoplastic material. Preferred materials include polycarbonate containing glass fibers (such as no. DF-1004 resin from LNP) and unfilled polycarbonate (such as "LEXAN" brand, No. HP1; from GE).

Preferably, the body 12 has an outer, buccolabial surface 27 that is relatively rough in surface texture in comparison to conventional plastic brackets, in order to enable the body 12 to present a pleasing, translucent appearance. The rough outer surface 27 is especially advantageous when the body 12 is made of an unfilled plastic with relatively low haze values (e.g., less than about 30%) such as unfilled polycarbonate that might otherwise present a transparent appearance. Haze is that percentage of transmitted light which in passing through a specimen deviates from the incident beam by forward scattering, and is measured according to the procedure set out in ANSI/ASTM D 1003 with a sample thickness of 0.125 in. (3.2 mm). The rough outer surface 27 diminishes specular reflection such as is sometimes observed in connection with transparent plastic brackets.

The rough outer surface 27 diffuses light passing through the body 12 and effectively masks the framework 14 from view. Further, the translucent appearance of the body 12 matches the translucent appearance presented by translucent polycrystalline ceramic brackets (such as "TRANSCEND"

brand brackets from 3M Unitek). As a result, the appliance 10 may be used interchangeably with such ceramic brackets without undue noticeable differences in appearance.

The outer surface 27 has a surface roughness of greater than 43 microinches $R_A$ (arithmetic mean roughness), and more preferably a surface roughness of greater than about 50 microinches $R_A$. The rough outer surface 27 may be made by directing a stream of abrasive material (such as 150 micrometer alumina grit using a MICROBLASTER brand sandblaster) toward the buccolabial surface 27 of the body 12. Alternatively, the surfaces of the forming tooling for making the body 12 are roughened in such a fashion that the buccolabial surface of the body 12 once molded has a similar roughened characteristic.

The outer surface 27 has a roughness of greater than 37 $R_A$ when the haze value of the material is less than about 30% (test specimen thickness of 0.125 inch, or 3.2 mm), more preferably when the haze value is less than about 5% and most preferably when the haze value is about 2% or less. Preferably, the luminous transmittance of the plastic body (when measured according to ANSI/ASTM D 1003-61 and the test specimen thickness is 0.125 inch or 3.2 mm) is greater than about 5%, more preferably greater than about 70% and most preferably equal to about 88% or greater.

Figure 5:
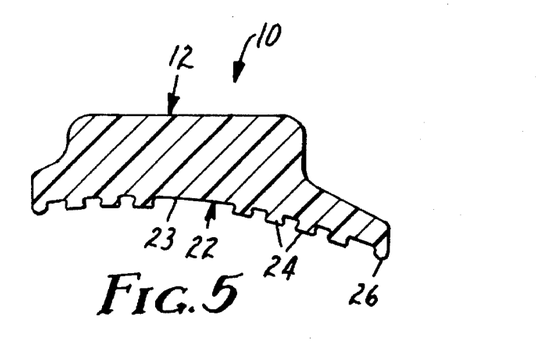
FIG. 5 is a view somewhat similar to FIG. 4 except that projections of the bonding base have been deformed to provide a mechanical interlock with orthodontic adhesive.

The bond strength of the appliance 10 is enhanced by deforming the projections 24 in lateral directions to provide overhanging regions. The projections 24 are deformed by applying heat to an outer portion of the projections 24 to soften the outer portions and move the outer portions in lateral directions (i.e., laterally of a central, labiolingual reference axis of each projection 24). When the body is made of polycarbonate, heat is applied to the outer portion of the projections 24 until the temperature of the outer portions is above the glass transition temperature of polycarbonate. As the outer portions are softened and moved, the projections 24 change from the peg-shaped appearance illustrated in FIG. 4 to the flattened knob-like or mushroom cap appearance that is illustrated in FIG. 5.

Once deformed, the projections 24 each present an overhanging region that is wider in lateral direction (i.e., in directions perpendicular to the aforementioned labiolingual reference axis) than the width of underlying portions of the shank of the respective projection 24. Each overhang presents an undercut that is adapted to receive orthodontic adhesive when the appliance 10 is bonded to the tooth. Once the adhesive has hardened, the adhesive together with the overhanging portions of the projections 24 establish an interlocking, structural connection that has significant strength and is suitable for the forces normally encountered in orthodontic treatment.

Preferably, the appliance 10 is pretreated by applying a pretreating solution comprising i) a polymerizable component, ii) a solvent capable of at least partially solubilizing the plastic dental appliance, and iii) a photoinitiator system to the bonding base 22; and curing the pretreating solution by exposure to actinic radiation. Components i) and ii) may be the same or different materials. A conventional adhesive (such as "CONCISE" brand or "TRANSBOND XT" brand adhesive from 3M Unitek) can then be used to bond the appliance 10 to the selected tooth. Optionally, the appliance 10 may additionally be precoated with an orthodontic adhesive and packaged accordingly.

The polymerizable component optionally may be selected from any materials suitable for use as dental adhesive resins that will alone or in combination with other materials act to at least partially solubilize the plastic dental appliance. Examples of such materials are acrylates and methacrylates, such as C 1–6 alkyl acrylates and methacrylates and C 1–12 alkoxyalkyl acrylates and methacrylates, and more preferably C 1–2 alkyl acrylates and methacrylates and C 1–4 alkoxyalkyl acrylates and methacrylates. Other preferred polymerizable components are monomers traditionally used in dental materials, such as the dimethacrylate derived from the reaction between methacrylic acid and the diglycidyl ether of bisphenol A ("Bis-GMA"), tetraethylene glycol dimethacrylate, Bisphenol A diethyleneglycol dimethacrylate ("Bis-EMA") and triethylene glycol dimethacrylate ("TEDGMA"). Polymers, such as polymethyl methacrylate, may also be incorporated in the pretreatment compositions as appropriate.

As an example, a pretreating solution is made by mixing three parts of methyl methacrylate (MMA) and one part of Bis-GMA until homogeneous, and then dissolving 0.375% camphorquinone (CPQ) and 1% ethyl-4-dimethyl-amino benzoate (EDMAB) in the resin mixture. Approximately 2.5 microliters of solution is applied to each appliance. Each appliance is allowed to dry for 2 to 3 minutes and then cured by exposure to a dental curing light (such as ORTHOLUX brand curing light from 3M Unitek) for 10 seconds. A conventional adhesive (such as "CONCISE" brand or "TRANSBOND XT" brand from 3M Unitek) can then be used to bond the appliance to the selected tooth.

Figure 6:
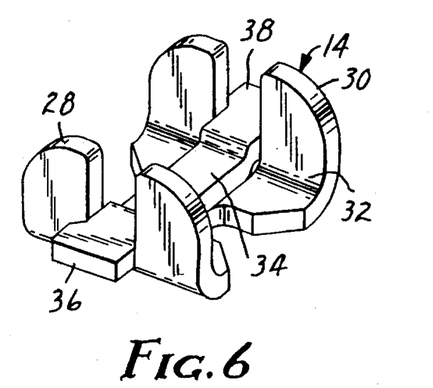
FIG. 6 is a perspective view of a framework of the appliance depicted in FIGS. 1–5.
Figure 7:
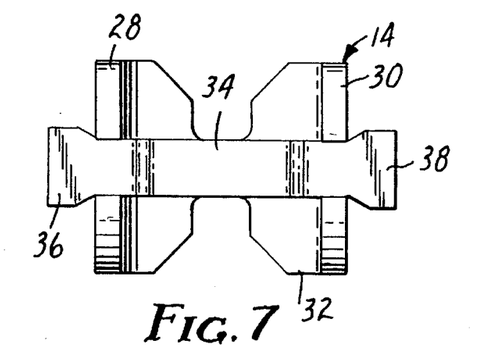
FIG. 7 is a plan view looking toward a buccolabial side of the framework shown in FIG. 6.
Figures 8, 9, 10, 11, 12:
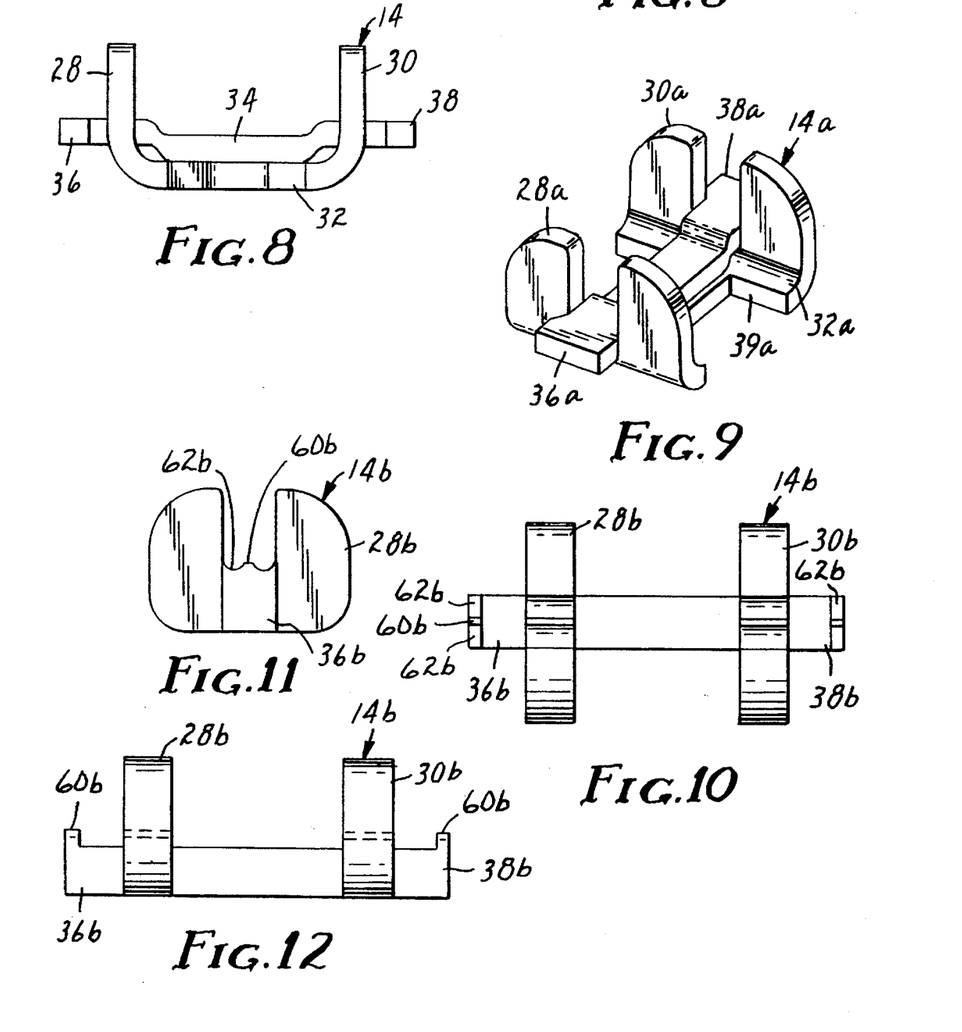
FIG. 8 is a side view of the framework shown in FIGS. 6–7.
FIG. 9 is a perspective view of a framework according to an alternate construction for the appliance shown in FIGS. 1–5.
FIG. 10 is a front view looking toward a buccolabial side of a framework according to yet another construction for the appliance illustrated in FIGS. 1–5.
FIG. 11 is an end view of the framework shown in FIG. 10.
FIG. 12 is a side view of the framework depicted in FIGS. 10–11.

The framework 14 has a generally H-shaped configuration, and is shown alone in FIGS. 6–8. The framework 14 is optionally coated or otherwise colored by ink or paint (such as an epoxy paint), porcelain or other material to match the color of the tooth or the color of the plastic material. The coating may be applied by a wet or a dry electrostatic coating process.

The framework 14 includes a mesial portion 28 that extends in the mesial tiewing section 16 in a transverse direction with respect to the longitudinal axis of the archwire slot 20. The framework 14 also includes a distal portion 30 that extends in the distal tiewing section 18 in a transverse direction with respect to the longitudinal axis of the archwire slot "Transverse" as used herein, means ninety degrees plus or minus twenty degrees, as angles other than perpendicular may be useful for "angulated" brackets. Preferably, however, the framework 14 has a shape and size similar to that shown in the drawings so that a single framework may be used with a variety of both angulated as well as non-angulated brackets.

The mesial portion 28 and the distal portion 30 each include an occlusally-facing edge that is coplanar with a gingival side of the archwire slot 20. The portions 28, 30 also each include a gingivally-facing edge that is coplanar with an occlusal side of the archwire slot 20.

In the particular embodiment shown in FIGS. 6–8, the framework 14 is made of two initially separate pieces: a first, generally "U"-shaped piece 32 having opposed, parallel legs that present the mesial and distal portions 28, 30, and a second piece 34 that is connected to the first piece 32 and extends through channels of the first piece 32. The first piece 32 is connected to the second piece 34 by use of an interference fit in areas where the second piece 34 extends through channels of the first piece 32. Optionally, the first piece 32 and second piece 34 are connected together by spot welding or by brazing.

The second piece 34 includes a first end portion 36 that is located mesially of the mesial portion 28 and a second end portion 38 that is located distally of the distal portion 30. As shown in the drawings, the first end portion 36 extends between the mesial portion 28 and a mesial side of the plastic body 12 and the second end portion 38 extends between the distal portion 30 and a distal side of the body 12. Each of the end portions 36, 38 have a buccolabially-facing surface that is located on and coplanar with a lingual side of the archwire slot 20. The end portions 36, 38 provide bearing surfaces for the archwire when received in the archwire slot 20. The end portions 36, 38 are especially advantageous in providing control of rotation of the associated tooth when attempts are made to rotate the tooth about its long axis.

As illustrated in FIGS. 6–8, each of the end portions 36, 38 has an occlusally-extending section and a gingivally-extending section that extends beyond occlusal and gingival sides respectively of the portion of the archwire slot 20 that is defined by the plastic body 12. Such sections are embedded within the body 12 and help anchor the framework 14 and particularly the second piece 34 in the body 12 so that the second piece 34 does not separate from the first piece 32 or the body 12 under normal, expected conditions.

An intermediate portion of the second piece 34, located between the mesial portion 28 and the distal portion 30, is preferably not exposed and instead is covered by a portion of the body 12, such that a buccolabially-facing surface of such intermediate portion is spaced in a lingual direction from the lingual side of the archwire slot 20. However, regardless of whether or not such plastic covering is absent (and regardless of whether or not the buccolabially-facing surface of the intermediate portion is coplanar with the buccolabially-facing surfaces of the end portions 36, 38), the buccolabially-facing surfaces of the end portions 36, 38 serve as (as shall be deemed as) the lingual side of at least a portion of the archwire slot.

An alternate framework 14a is illustrated in FIG. 9, and is substantially the same as the framework 14 described above in connection with FIGS. 6–8. However, a first piece 32a of the framework 14a has an intermediate section with a U-shaped notch 39a that is greater than the corresponding notch formed in the intermediate portion of the first piece 32 of framework 14, in order to reduce the visibility of the framework 14 and improve aesthetics of the appliance 10 in instances where the body 12 is made of a transparent or translucent material.

Another alternative framework 14b is illustrated in FIGS. 10–12. The framework 14b is preferably an integral, one-piece construction made by a metal injection molding process, by machining, or by extrusion or cold drawn forming followed by machining.

The framework 14b has a mesial portion 28b, a distal portion 30b and end portions 36b, 38b. The end portions 36b, 38b have a buccolabially-facing edge with a platform 60b that is raised in a buccolabial direction on a lingual side of the archwire slot for engagement with the archwire. Each buccolabial edge has a pair of lingually-extending recesses 62b disposed on opposite, occlusal and gingival sides of the platform, so that only a portion of the end portions 36b, 38b are in contact with the archwire. Moreover, each platform 60b is spaced from the respective mesial and distal portions 28b, 30b by a connector portion that is embedded in the plastic body.

The mesial and distal portions 28b, 30b also each have a raised, buccolabially-facing platform 60b that is located on the lingual side of the archwire slot. The portions 28b, 38b have lingually-extending recesses located on opposite sides of the platform. The platforms 60b and recesses 62b of the end portions 36b, 38b and the mesial and distal portions 28b, 30b have identical double-"U"-shaped configurations when viewed along the length of the archwire slot as shown in FIG. 11, although other configurations are also possible.

Figure 13:
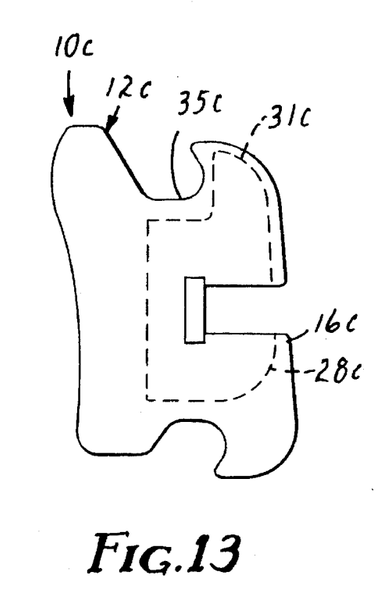
FIG. 13 is an end elevational view of an orthodontic appliance with yet another framework.
Figure 14:
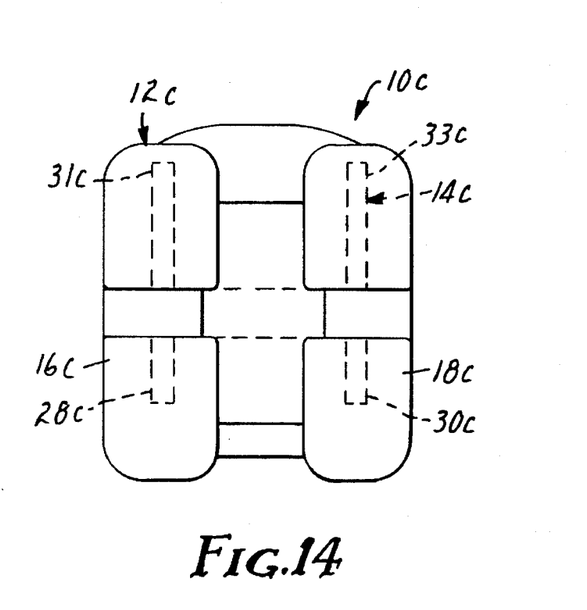
FIG. 14 is a front view looking toward a buccolabial side of the appliance illustrated in FIG. 13.

The framework 14c of an appliance 10c that is depicted in FIGS. 13–14 is somewhat similar to the framework 14 shown in FIGS. 6–8. However, a mesial portion 28c and a distal portion 30c of the framework 14c have sections 31c, 33c respectively that extend into occlusal regions of mesial and distal tiewing sections 16c, 18c of the appliance 10c. Both sections 31c, 33c extend occlusally of an occlusal tiewing undercut 35c that is shaped to receive an archwire ligature.

The sections 31c, 33c effectively prevent undue wear of the tiewing sections 16c, 18c in instances where the patient's opposing dentition frequently contacts the appliance 10c. In such instances, the portion of the body 12c initially covering the sections 31c, 33c may wear away, but the sections 31c, 33c will resist wear and enable the tiewing sections 16c, 18c to serve their intended functions.

Figure 15:
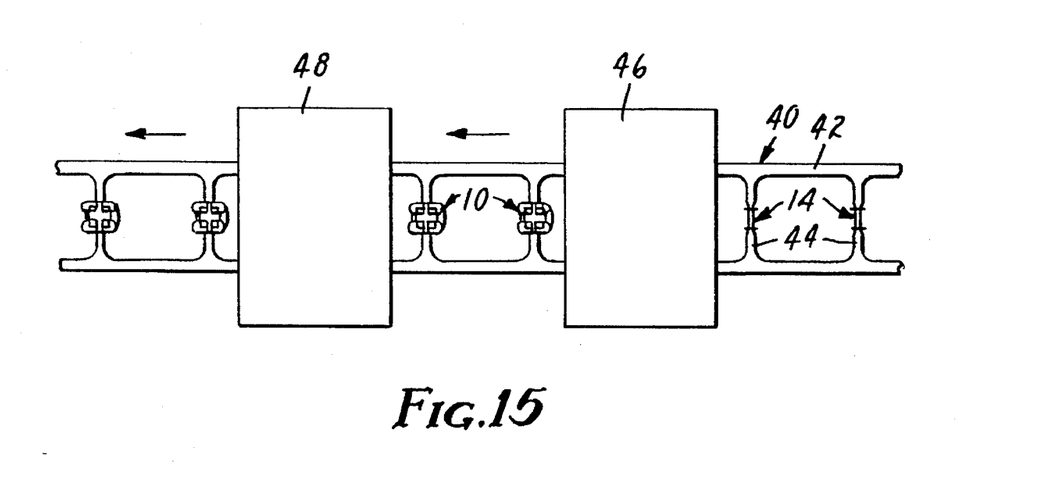
FIG. 15 is a reduced, bottom view in partially schematic form of method steps for making an appliance in accordance with the present invention.

FIG. 15 illustrates a method of making orthodontic appliances such as the appliance 10 in accordance with the invention. As shown, a "ladder"-shaped metal carrier or lattice 40 is provided and includes two side members 42 that are coupled together at a number of spaced apart intervals by a number of connecting members 44. The lattice 40 is made by a metal stamping process using a 0.01 inch (0.25 mm) thick sheet of type 17-4 PH stainless steel. Other possible materials include type 301 stainless steel, a stainless steel that is hardenable by heat treatment, or a cold-worked austenitic material.

Each of the connecting members 44 includes a middle portion that provides part or all of a framework, such as second piece 34 of the framework 14. Each first piece 32 is assembled to a second piece 34. The lattice 40 is advanced from a feed roll to body forming tooling 46, such as a die for injection molding plastic brackets.

In the tooling 46, a quantity of molding material to make the appliance body 12 is placed about the assembled framework 14. In the case of plastic bracket molding, the pressure and temperature within the forming tooling 46 are raised to levels sufficient to injection mold the appliance body 12. After solidification and opening of the tooling 46, the lattice 40 is incrementally advanced in order to bring each appliance 10 to a bonding base projection forming tooling 48. In the tooling 48, a heated mandrel is moved toward the bonding base 22 of each approaching appliance 10 in order to soften outer portions of the projections 24 and move the projections 24 in lateral directions to present overhanging regions.

Figure 16:
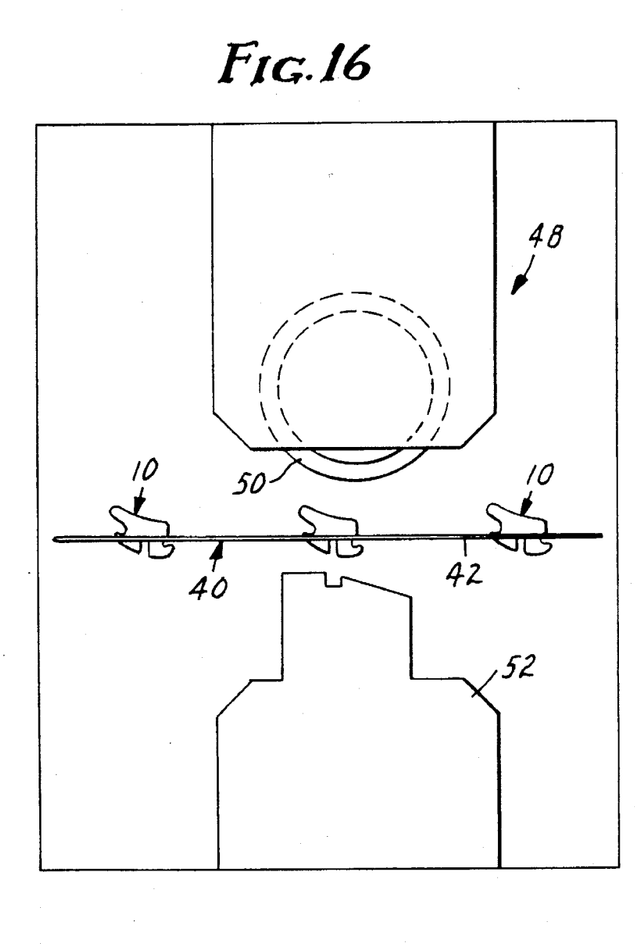
FIG. 16 is a fragmentary, side elevational view of one of the steps of the method shown in FIG. 15 that is preliminary to a projection forming step.
Figure 17:
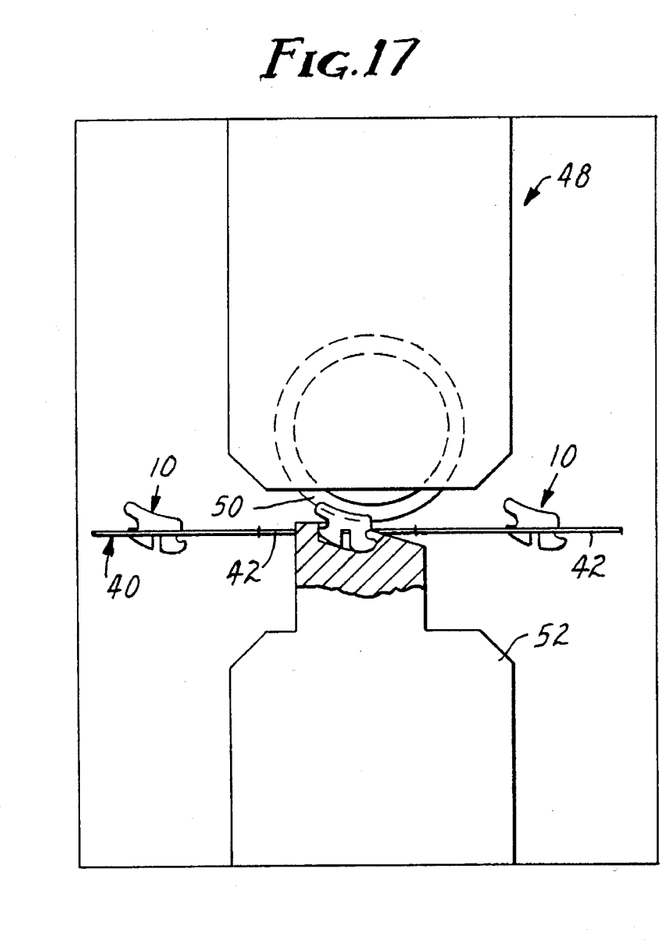
FIG. 17 is a view somewhat similar to FIG. 16 except that a bracket support and a mandrel have engaged one of the appliances on opposite sides in order to carry out the projection forming step.

FIGS. 16–17 include additional details of the projection forming tooling 48. The mandrel 50 has a compound curved convex surface that matches the shape of the tooth to which the appliance 10 is to be bonded, and that also matches a curved reference plane that lies across the outer end of each undeformed projection 24 as illustrated in FIG. 4. Preferably, rim 26 has a uniform height such that the outer, lingual edge of the rim 26 is spaced from such reference plane in FIG. 4 an equal distance along the entire extent of the rim 26.

The buccolabial side of the appliance 10 is supported by a support 52 that rises to contact the appliance 10 as the mandrel 50 descends. The support 52 includes a nest that is shaped to complementally reveive the appliance 10. Optionally, the support 52 may include movable arms that also engage the appliance 10 to keep it steady during deforming of the projections 24.

As the mandrel 50 advances toward the body 12, the mandrel 50 contacts and deforms the outer portion of each projection 24 until such outer portions take on the configuration as illustrated in FIG. 5. As soon as the mandrel 50 contacts the rim 26, however, further advancement of the mandrel 50 is interrupted and the mandrel 50 is then withdrawn in an opposite direction to enable the projections 24 to cool and harden. The rim 26 serves as a precise stop for advancement of the mandrel 50.

Optionally, the convex head of the mandrel 50 that contacts the appliance 10 is substantially larger in surface area than the area of the bonding base 22, and is mounted on a holder that enables different regions of the head to be used for forming the bonding base 22. In this manner, if one region is worn, the head can be adjusted to bring another region into use.

Referring again to FIG. 15, the lattice 40 is again incrementally advanced once the projections 24 of the bonding base 22 have been deformed in the forming tooling 48 to establish the overhanging regions. The lattice 40 is then wound about a windup roll, or advanced to other processing operations such as a sandblasting operation for roughening the outer surface 27.

Preferably, the connecting member 44 includes two lines of weakness that are located within the body 12 and immediately adjacent the mesial side of the mesial section 16 and the distal side of the distal section 18 after the body 12 is formed. The appliance 10 is separated from the lattice 40 by bending the exposed portions of the connecting member 44. Advantageously, the member 44 fractures along the lines of weakness such that the fractured edges are located inwardly of the sections 16, 18.

EXAMPLE

The surface roughness was measured and the visual characteristics were assessed of unfilled polycarbonate test samples as well as orthodontic brackets that have been sold in the market. The unfilled polycarbonate test samples were made from "LEXAN" brand polycarbonate (from G.E.) and were roughened on one side.

Samples 1–3 were roughened using a sandblaster ("MICROBLASTER"; from Comco). The sandblasting was carried out using 150 micrometer alumina grit with the cutting speed set to the "medium" range. The samples were waved by hand in front of the sandblaster, and increased surface roughness was obtained by increasing the exposure time. Sample no. 4 was roughened by wet sanding a similar unfilled polycarbonate blank with 180 grit sandpaper. The samples were visually characterized for any translucent appearance, and the results are set out in Table 1.

Surface roughness measurements were made on samples 1–4 using a "HOMMEL" brand profilometer (model no. T1000; from Hommelwerke). The profilometer tip (part no. TE-1 from Hommelwerke) was scanned 1.5 mm across each sample. Surface roughness measurements are also set out in Table 1 and are arithmetic mean roughness values ($R_A$) according to the Hommel instruction manual (which refers to DIN 4768/1, DIN 4762/1 E and ISO/DIS 4287/1).

TABLE 1

| Sample | Roughness µ-in. $R_A$ | Roughness micron $R_A$ | Appearance |
| --- | --- | --- | --- |
| 1 | 37 | .94 | marginally translucent |
| 2 | 56 | 1.42 | translucent |

TABLE 1-continued

| Sample | Roughness µ-in. $R_A$ | Roughness micron $R_A$ | Appearance |
| --- | --- | --- | --- |
| 3 | 80 | 2.03 | translucent |
| 4 | 53 | 1.35 | translucent |

For comparison, the surface roughness of commercial plastic brackets was measured using the "HOMMEL" brand profilometer and tip described above. For each bracket, the tip was scanned 1.5 mm across a non-lingual surface that was unobstructed by surface features (such as molding gates or ejector pin marks). (Those brackets that are filled would have a haze value for the plastic body material of significantly greater than 30%). The results of the measurements are set out in Table 2.

TABLE 2

| Bracket | Filler | Resin | Appearance | Roughness ($R_A$) µ-inch | micron |
| --- | --- | --- | --- | --- | --- |
| 3M Unitek (007–380; obsolete) | no | poly-carbonate | transparent | 20 | 0.50 |
| CDB Reflections | no | poly-urethane | transparent | 19 | 0.48 |
| American Silkon | yes | poly-carbonate | translucent | 25 | 0.64 |
| Ormco Spirit | yes | poly-carbonate | translucent | 39 | 0.99 |

The data show that for brackets made of unfilled plastic materials, a surface roughness somewhat greater than 37 microinch $R_A$ (0.94 micron $R_A$) is desirable for presenting a translucent appearance.

Although the preferred embodiments of our invention have been described above in detail, it should be apparent to those skilled in the art that many variations and modifications are possible without departing from the spirit of our invention. Accordingly, the scope of the invention should not be deemed limited to the embodiments described above, but only by a fair reading of the claims that follow along with their equivalents.

We claim:

1. A plastic orthodontic bracket comprising:

a plastic body having a mesial tiewing section with a mesial side, a distal tiewing section with a distal side and an elongated archwire slot extending through said mesial tiewing section and said distal tiewing section, said archwire slot including a lingual side; and a metallic framework partially embedded in said plastic body, said framework including a mesial portion extending in said mesial tiewing section in a transverse direction with respect to the longitudinal axis of said archwire slot and a distal portion extending in said distal tiewing section in a transverse direction with respect to the longitudinal axis of said archwire slot, said framework including an intermediate portion interconnecting said mesial portion and said distal portion, said framework including a first end portion extending between said mesial portion and said mesial side and a second end portion extending between said distal portion and said distal side, said first end portion and said second end portion each having a buccolabially-facing surface that is coplanar with said lingual side of said archwire slot.

2. The orthodontic bracket of claim 1, wherein said intermediate portion of said framework has a buccolabially-facing surface that is at least partially embedded in said plastic body and is spaced lingually from said lingual side of said archwire slot.

3. The orthodontic bracket of claim 1, wherein said archwire slot includes an occlusal side and a gingival side, wherein said mesial portion and said distal portion of said framework each include an occlusally-facing edge that is coplanar with said gingival side of said archwire slot and a gingivally-facing edge that is coplanar with said occlusal side of said archwire slot.

4. The orthodontic bracket of claim 3, wherein said first end portion extends between said occlusally-facing edge of said mesial portion and said gingivally-facing edge of said mesial portion, and wherein said second end portion extends between said occlusally-facing edge of said distal portion and said gingivally-facing edge of said distal portion.

5. The orthodontic bracket of claim 1, wherein said first end portion is coupled to said mesial portion by a first connector portion that is embedded in said plastic body, and wherein said second end portion is coupled to said distal portion by a second connector portion that is embedded in said plastic body.

6. The orthodontic bracket of claim 1, wherein said first end portion is directly adjacent said mesial portion and said second end portion is directly adjacent said distal portion.

7. A plastic orthodontic bracket comprising:

a plastic body having a mesial tiewing section, a distal tiewing section and an elongated archwire slot extending through said mesial tiewing section and said distal tiewing section, said archwire slot including a lingual side; and a metallic framework partially embedded in said plastic body, said framework including a mesial portion extending in said mesial tiewing section in a transverse direction with respect to the longitudinal axis of said archwire slot and a distal portion extending in said distal tiewing section in a transverse direction with respect to the longitudinal axis of said archwire slot, said framework including an intermediate portion interconnecting said mesial portion and said distal portion, said framework including a first end portion located mesially of said mesial portion and a second end portion located distally of said distal portion, said first end portion and said second end portion each having a buccolabially-facing surface that is coplanar with said lingual side of said archwire slot, wherein said archwire slot has an occlusal side and a gingival side, and wherein said first end portion and said second end portion each have an occlusally-extending section that extends beyond said occlusal side and a gingivally-extending section that extends past said gingival side.

8. The orthodontic bracket of claim 7, wherein said occlusally-extending sections and said gingivally-extending sections are embedded in said plastic body.

9. A plastic orthodontic bracket comprising:

a plastic body having a mesial tiewing section, a distal tiewing section and an elongated archwire slot extending through said mesial tiewing section and said distal tiewing section, said archwire slot including a lingual side; and a metallic framework partially embedded in said plastic body, said framework including a mesial portion extending in said mesial tiewing section in a transverse direction with respect to the longitudinal axis of said archwire slot and a distal portion extending in said distal tiewing section in a transverse direction with respect to the longitudinal axis of said archwire slot, said framework including an intermediate portion interconnecting said mesial portion and said distal portion, said framework including a first end portion located mesially of said mesial portion and a second end portion located distally of said distal portion, said first end portion and said second end portion each having a buccolabially-facing surface that is coplanar with said lingual side of said archwire slot, wherein said first end portion and said second end portion each have a buccolabially-facing edge having a platform that is raised in a buccolabial direction presenting said buccolabial surface, each buccolabial edge having a recess next to said platform of the respective end portion that is located lingually of said platform of the respective end portion.

10. A plastic orthodontic bracket comprising:

a plastic body having a mesial tiewing section, a distal tiewing section and an elongated archwire slot extending through said mesial tiewing section and said distal tiewing section, said archwire slot including a lingual side; and a metallic framework partially embedded in said plastic body, said framework including a mesial portion extending in said mesial tiewing section in a transverse direction with respect to the longitudinal axis of said archwire slot and a distal portion extending in said distal tiewing section in a transverse direction with respect to the longitudinal axis of said archwire slot, said framework including an intermediate portion interconnecting said mesial portion and said distal portion, said framework including a first end portion located mesially of said mesial portion and a second end portion located distally of said distal portion, said first end portion and said second end portion each having a buccolabially-facing surface that is coplanar with said lingual side of said archwire slot, wherein said mesial portion and said distal portion each include a buccolabially-facing edge with a raised, buccolabially-facing surface that is coplanar with said lingual side of said archwire slot and a recess next to said raised surface of the respective end portion that is located lingually of said raised surface of the respective end portion.

11. An orthodontic appliance comprising a plastic body having a mesial tiewing section, a distal tiewing section and an archwire slot extending through said mesial tiewing section and said distal tiewing section, said body including an outer, buccolabially-facing surface having a surface roughness of greater than about 43 microinches $R_A$.

12. The orthodontic appliance of claim 11, wherein said outer surface has a surface roughness of greater than about 50 microinches $R_A$.

13. The orthodontic appliance of claim 11 and including a metallic framework at least partially embedded in said plastic body.

14. The orthodontic appliance of claim 13, wherein said archwire slot includes a lingual side, and wherein at least one portion of said framework is coplanar with said lingual side.

15. An orthodontic appliance comprising a plastic body having a mesial tiewing section, a distal tiewing section and an archwire slot extending through said mesial tiewing section and said distal tiewing section, said body including an outer, buccolabially-facing surface having a surface roughness of greater than about 37 microinches $R_A$, said body having a haze value of less than about 30%.

16. The orthodontic appliance of claim 15, wherein said outer surface has a surface roughness of greater than about 43 microinches $R_A$.

17. The orthodontic appliance of claim 15, wherein said haze value is less than about 5%.

18. The orthodontic appliance of claim 15 and including a metallic framework at least partially embedded in said plastic body.

* * * * *